United States Patent
Kim et al.

(10) Patent No.: US 11,414,685 B2
(45) Date of Patent: *Aug. 16, 2022

(54) **METHOD FOR PREPARING D-PSICOSE USING MICROORGANISM OF GENUS *KAISTIA***

(71) Applicant: CJ CHEILJEDANG CORPORATION, Seoul (KR)

(72) Inventors: Su Jin Kim, Suwon-si (KR); Young Mi Lee, Suwon-si (KR); Yang Hee Kim, Suwon-si (KR); Seong Bo Kim, Seongnam-si (KR); Seung Won Park, Yongin-si (KR); Seong Jun Cho, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 180 days.

This patent is subject to a terminal disclaimer.

(21) Appl. No.: 16/461,308

(22) PCT Filed: Nov. 15, 2017

(86) PCT No.: PCT/KR2017/012971
§ 371 (c)(1),
(2) Date: May 15, 2019

(87) PCT Pub. No.: WO2018/093154
PCT Pub. Date: May 24, 2018

(65) Prior Publication Data
US 2020/0032307 A1 Jan. 30, 2020

(30) Foreign Application Priority Data
Nov. 16, 2016 (KR) .................. 10-2016-0152948

(51) Int. Cl.
*C12P 19/02* (2006.01)
*C12N 1/20* (2006.01)
*C12R 1/01* (2006.01)

(52) U.S. Cl.
CPC .............. *C12P 19/02* (2013.01); *C12N 1/20* (2013.01); *C12N 1/205* (2021.05); *C12R 2001/01* (2021.05)

(58) Field of Classification Search
CPC . C12P 19/02; C12P 19/24; C12N 1/20; C12N 1/205; C12R 2001/01; C12Y 501/03
See application file for complete search history.

(56) References Cited

U.S. PATENT DOCUMENTS

2016/0244770 A1* 8/2016 Karas ..................... C12N 15/79
2019/0136276 A1* 5/2019 Kim ....................... C12N 9/1205

FOREIGN PATENT DOCUMENTS

| CN | 105802897 A | 7/2016 | |
|---|---|---|---|
| JP | 09-056390 A | 3/2009 | |
| KR | 10-2011-0035805 A | 4/2011 | |
| KR | 10-2016-0081722 A | 7/2016 | |
| KR | 10-1807507 B1 | 12/2017 | |
| WO | WO-2017111563 A1 * | 6/2017 | ............... C07H 3/02 |

OTHER PUBLICATIONS

Lee, H et al. *Kaistia granuli* sp. nov., isolated from anaerobic granules in an upflow anaerobic sludge blanket reactor. International Journal of Systematic and Evolutionary Microbiology. 2007. 57: 2280-2283. (Year: 2007).*
V Bilik, "Reactions of Saccharides Catalyzed by Molybdate ions. III. Preparation of L-Glucose by Epimerization of L-Mannose or L-Mannose Phenylhydrazone," Chem. Zvesti 28, pp. 187-189 (1972).
International Search Report dated Feb. 14, 2018 in connection with PCT International Application No. PCT/KR2017/012971.
Jin, Long et al., "*Kaistia defluvii* sp. Nov., isolated from river sediment", International Journal of Systematic and Evolutionary Microbiology (2012), 62, pp. 2878-2882.
Landis W. Doner, "Isomerization of D-Fructose by Base: Liquid-Chromato-Graphic Evaluation and the Isolation of D-Pscicose", Carbohydrate Research, 70 (1979), pp. 209-216.
Weon, Hang-Yeon et al., "*Kaistia soli* sp. Nov., isolated from a wetland in Korea", International Journal of Systematic and Evolutionary Microbiology, 2008, vol. 58, pp. 1522-1524.
Written Opinion (form PCT/ISA/237) dated Feb. 14, 2018 in connection with PCT International Application No. PCT/KR2017/012971.
Office Action issued by the Argentina Patent Office regarding Argentina Application No. 20170103191, dated Jan. 13, 2022.
Oh, Deok-Kun, et al. (2007). D-Psicose production from D-fructose using an isolated strain, *Sinorhizobium* sp . . . World Journal of Microbiology and Biotechnology. 23. 559-563. 10.1007/s11274-006-9265-7.

* cited by examiner

*Primary Examiner* — Renee Claytor
*Assistant Examiner* — Susan E. Fernandez
(74) *Attorney, Agent, or Firm* — John P. White (57) ABSTRACT

Provided are a composition for preparing D-psicose comprising a microorganism of the genus *Kaistia*, and a method for preparing D-psicose using the same.

5 Claims, 5 Drawing Sheets
Specification includes a Sequence Listing.

FIG. 1

*Kaistia granuli* LIS1

FIG. 2

*Kaistia defluvii* LIS2

FIG. 3

*Kaistia granuli* KCTC12575

FIG. 4

*Kaistia defluvii* KCTC23766

FIG. 5

Kaistia geumhonensis KCTC12849

FIG. 6

Kaistia adipata KCTC12095

FIG. 7

Kaistia dalseonensis KCTC12850

FIG. 8

Kaistia hirudinis DSM25966

FIG. 9

*Kaistia soli* DSM19436

FIG. 10

*Kaistia terrae* DSM21341

METHOD FOR PREPARING D-PSICOSE USING MICROORGANISM OF GENUS KAISTIA

CROSS-REFERENCE TO RELATED APPLICATIONS

This application is a § 371 national stage of PCT International Application No. PCT/KR2017/012971, filed Nov. 15, 2017, claiming priority of Korean Patent Application No. KR 10-2016-0152948, filed Nov. 16, 2016, the contents of each of which are hereby incorporated by reference into the application.

REFERENCE TO A SEQUENCE LISTING

This application incorporates-by-reference nucleotide and/or amino acid sequences which are present in the file named "191017_90979_Sequence_Listing_CAS.txt", which is 8.16 kilobytes in size, and which was created Oct. 17, 2019 in the IBM-PC machine format, having an operating system compatibility with MS-Windows, which is contained in the text file which is being submitted as part of this application.

TECHNICAL FIELD

The following disclosure relates to a method for preparing a D-psicose using a microorganism of the genus Kaistia.

BACKGROUND

D-psicose (hereinafter referred to as "psicose") is a monosaccharide known as a rare sugar present in the natural world in a very small amount. It has almost zero calorie while having nearly 70% sweetness of sugar and has received a lot of attention as a new food ingredient due to its functionalities such as inhibition of blood glucose, and inhibition of lipid synthesis, etc.

Due to these characteristics, psicose is considered to be used as a sweetener substitute for sugar in various foods. However, there is an increasing need for a method for efficiently preparing psicose since it exists in a very small amount in the natural world.

A known method for preparing psicose comprises a method for utilizing catalysis of molybdate ions (Bilik, V., Tihlarik, K., 1973, Reaction of Saccharides Catalyzed by Molybdate Ions. IX. Epimerization of Ketohexoses. Chem. Zvesti. 28:106-109), A Chemical Method for Preparing Psicose from D-Fructose by Heating Ethanol and Triethylamine Together (Doner, L. W., 1979, Isomerization of D-Fructose by Base: Liquid-Chromatographic Evaluation and The Isolation of D-Psicose. Carbohydr. Res. 70:209-216), and A Biological Method for Preparing Psicose from D-Fructose Using a Microorganism that Produces D-Psicose 3-Epimerase (Korean Patent Laid-Open Publication No. 10-2011-0035805). Preparation of psicose by the chemical method has problems in that a large amount of byproducts occur, and thus, it is required to perform a complicated purification. Further, the biological method also has problems in that thermal stability is not high and the preparation cost is high, and thus there is a need to provide a new microorganism being able to produce psicose from D-fructose.

Under these circumstances, the present inventors have made a lot of effort to develop a new microorganism being able to produce psicose, and as a result, confirmed that when the microorganism of the genus Kaistia was used, psicose can be produced from D-fructose and completed the present invention.

Technical Problem

An embodiment of the present invention is directed to providing a composition for preparing psicose comprising a microorganism of the genus Kaistia.

Another embodiment of the present invention is directed to providing a method for preparing psicose comprising: contacting the microorganism of the genus Kaistia or the composition for preparing psicose comprising the microorganism of the genus Kaistia with D-fructose.

Another embodiment of the present invention is directed to providing a microorganism of the genus Kaistia useful for preparation of psicose.

Technical Solution

According to an exemplary embodiment of the present invention, there is provided a composition for preparing psicose comprising: a microorganism of the genus Kaistia.

The microorganism of the genus Kaistia of the present invention may comprise any microorganism without limitation as long as it has an ability to convert D-fructose to D-psicose. In an exemplary embodiment of the present invention, the microorganism of the genus Kaistia of the present invention may be at least one microorganism of the genus Kaistia selected from the group consisting of Kaistia granuli, Kaistia defluvii, Kaistia adipata, Kaistia geumhonensis, Kaistia dalseonensis, Kaistia hirudinis, Kaistia soli and Kaistia terrae. Specifically, the microorganism of the genus Kaistia of the present invention may be at least one microorganism of the genus Kaistia selected from the group consisting of Kaistia granuli LIS1 (accession number KCCM11916P), Kaistia defluvii LIS2 (accession number KCCM12020P), Kaistia granuli KCTC12575, Kaistia defluvii KCTC23766, Kaistia adipata KCTC12095, Kaistia geumhonensis KCTC12849, Kaistia dalseonensis KCTC12850, Kaistia hirudinis DSM25966, Kaistia soli DSM19436 and Kaistia terrae DSM21341.

In an exemplary embodiment, the microorganism of the genus Kaistia of the present invention may be a strain itself, a culture thereof, or a disruption of the microorganism. The culture or disruption of the microorganism of the genus Kaistia of the present invention may comprise a D-psicose-3-epimerase prepared from the microorganism of the genus Kaistia. In addition, the culture of the microorganism of the genus Kaistia of the present invention may or may not include the microorganism. Further, the disruption of the microorganism of the genus Kaistia of the present invention may be a disruption obtained by disrupting a microorganism of the genus Kaistia or a culture thereof, or a supernatant obtained by centrifuging the disruption.

In another exemplary embodiment of the present invention, the composition for preparing psicose of the present invention may further comprise: D-fructose.

In another exemplary embodiment of the present invention, the microorganism of the genus Kaistia of the present invention may be immobilized on a carrier to be used. An example of the carrier that is able to be used in the present invention includes, but is not limited to, agar, agarose, k-carrageenan, alginate or chitosan.

The composition for preparing the D-psicose of the present invention may further comprise a metal. More specifically, the metal of the present invention may be at least one metal selected from the group consisting of manganese, calcium, magnesium, iron, lithium and sodium. More specifically, the metal may be a metal ion or a metal salt, and more specifically, the metal salt may be at least one metal salt selected from the group consisting of LiCl, $Na_2SO_4$, $MgCl_2$, NaCl, $FeSO_4$, $MgSO_4$, $MnCl_2$, $MnSO_4$, and $CaCl_2$. The metal ion or the metal salt of the present invention may have a concentration of 0.1 mM to 10 mM, 0.1 mM to 7 mM, 0.1 mM to 4 mM, 0.5 mM to 10 mM, 0.5 mM to 7 mM, 0.5 mM to 4 mM, 1 mM to 10 mM, 1 mM to 7 mM, 1 mM to 4 mM, 2 mM to 10 mM, 2 mM to 7 mM or 2 mM to 4 mM.

According to another exemplary embodiment of the present invention, there is provided a method for preparing psicose, comprising: contacting a microorganism of the genus *Kaistia* or the composition for preparing psicose described in the present invention with D-fructose.

In an exemplary embodiment, the contacting of the present invention may be performed at pH of 5.0 to 9.0, at 40 to 90° C., and/or for 0.5 to 48 hours.

Specifically, the contacting of the present invention may be performed at pH 6.0 to 9.0, pH 7.0 to 9.0, pH 7.5 to 9.0, pH 6.0 to 8.5, pH 7.0 to 8.5, or pH 7.5 to 8.5.

In addition, the contacting of the present invention may also be performed at a temperature of 40° C. to 80° C., 40° C. to 75° C., 40° C. to 65° C., 50° C. to 90° C., 50° C. to 80° C., 50° C. to 75° C., 50° C. to 65° C., 55° C. to 90° C., 55° C. to 80° C., 55° C. to 75° C., 55° C. to 65° C., 60° C. to 90° C., 60° C. to 80° C., 60° C. to 75° C., 60° C. to 65° C., 65° C. to 90° C., 65° C. to 80° C. or 65° C. to 75° C.

In addition, the contacting of the present invention may be performed for 0.5 hour or more, 1 hour or more, 3 hours or more, 4 hours or more, 5 hours or more, or 6 hours or more, and/or 48 hours or less, 36 hours or less, 24 hours or less, 18 hours or less, 12 hours or less, 9 hours or less.

In another exemplary embodiment of the present invention, a weight ratio of the microorganism of the genus *Kaistia* to D-fructose of the present invention may be 1:1 to 1:5. Specifically, the weight ratio may be 1:1 to 1:4, 1:1 to 1:3, 1:2 to 1:5, 1:2 to 1:4, 1:2 to 1:3, or 1:2.5.

In another exemplary embodiment of the present invention, the preparation method of the present invention may further comprise: before, after or simultaneously with the contacting with the D-fructose, adding a metal.

In another exemplary embodiment of the present invention, the preparation method of the present invention may further comprise, after the contacting the D-fructose or the adding of the metal, isolating and/or purifying the psicose. The isolating and/or purifying of the present invention is not particularly limited, and may be performed by using a method generally used in the technical field of the present invention. For example, the isolating and/or purifying may be performed by one or more known methods such as dialysis, precipitation, adsorption, electrophoresis, ion exchange chromatography and fractional crystallization, etc., but is not limited thereto.

Further, the preparation method of the present invention may further comprise, before or after the isolating and/or purifying, performing decoloration and/or desalination, respectively. By performing the decolorization and/or desalination, it is possible to obtain more refined psicose without impurities.

In another exemplary embodiment of the present invention, the preparation method of the present invention may further comprise, after the contacting with the D-fructose, the adding of the metal, the isolating and/or purifying, or the performing of the decoloration and/or the desalination, crystallizing the D-psicose. The crystallization may be performed by using a crystallization method which is conventionally used. For example, the crystallization may be performed by using a cooling crystallization method.

In still another exemplary embodiment of the present invention, the preparation method of the present invention may further comprise, before the crystallizing, concentrating the psicose. The concentration may increase a crystallization efficiency.

In still another embodiment of the present invention, the preparation method of the present invention may further comprise, after the isolating and/or purifying, contacting an unreacted D-fructose with the microorganism of the genus *Kaistia*, or may further comprise, after the crystallizing, re-using a mother liquor from which crystallization is isolated in the isolating and/or purifying, or a combination thereof. Through the additional steps, the psicose may be obtained in a higher yield and an amount of D-fructose to be discarded may be reduced, thereby providing economic benefits.

The conversion rate from D-fructose to psicose according to the preparation method of the present invention may be 5% to 50%, 10% to 50%, 20% to 50%, 25% to 50%, 30% to 50% %, 5% to 40%, 10% to 40%, 20% to 40%, 25% to 40%, 30% to 40%, 5% to 35%, 10% to 35%, 20% to 35%, 25% to 35% or 30% to 35% based on weight.

The microorganism of the genus *Kaistia*, the D-fructose, the psicose, the metal and the carrier described in the method for preparing the psicose of the present invention are the same as described in the above-described exemplary embodiments.

According to still another exemplary embodiment of the present invention, there is provided a *Kaistia granuli* LIS1 strain deposited with Accession number KCCM11916P.

According to still another exemplary embodiment of the present invention, there is provided a *Kaistia defluvii* LIS2 strain deposited with Accession number KCCM12020P.

Effect of Invention

The microorganism of the genus *Kaistia* according to the present invention can convert D-fructose to psicose, at the same time has a thermal stability at a temperature of 50° C. or more, thereby making it possible to produce psicose on an industrial scale. Therefore, in case the microorganism of the genus *Kaistia* uses in production of psicose, psicose can be economically provided.

DETAILED DESCRIPTION OF EMBODIMENTS

Hereinafter, the present invention will be described in more detail by the following Examples. However, the present invention is not limited to Examples below, and it should be understood that various modifications and changes may be made by those skilled in the art within the scope and spirit of the present invention.

Throughout the specification of the present invention, unless otherwise noted, "%" used to denote a concentration of a specific material refers to a solid/solid (weight/weight) %, a solid/liquid (weight/volume) %, and a liquid/liquid (volume/volume) %.

EXAMPLES

Figure 1:
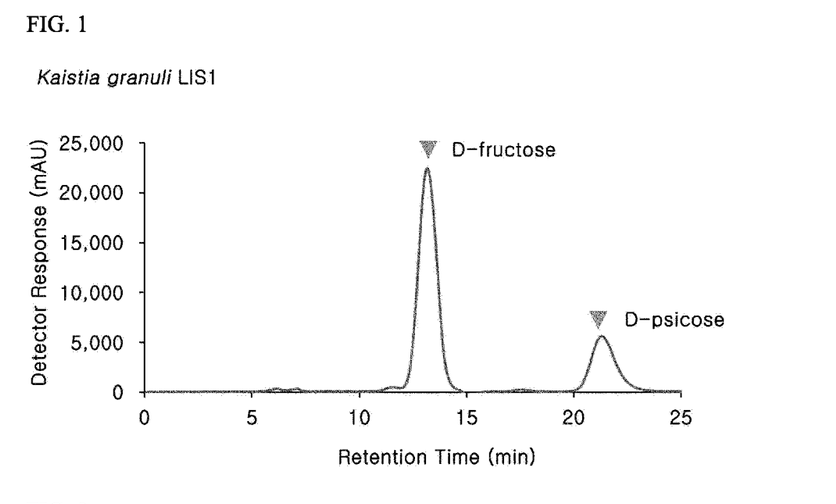
FIG. 1 is HPLC analytical data showing that it is possible to prepare psicose from D-fructose using *Kaistia granuli* LIS1, according to an exemplary embodiment of the present invention.
Figure 2:
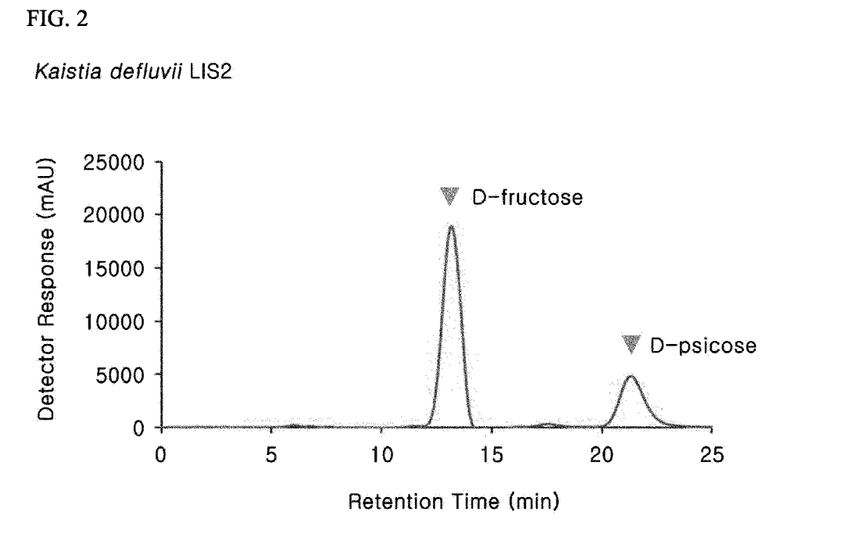
FIG. 2 is HPLC analytical data showing that it is possible to prepare psicose from D-fructose using *Kaistia defluvii* LIS2, according to an exemplary embodiment of the present invention.
Figure 3:
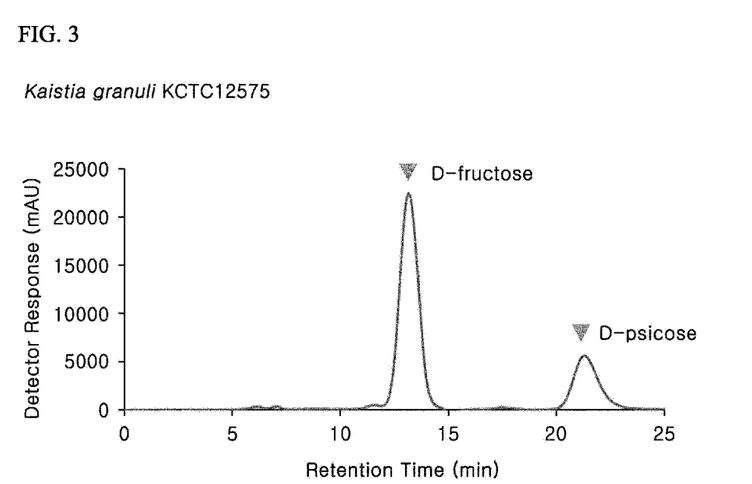
FIG. 3 is HPLC analytical data showing that it is possible to prepare psicose from D-fructose using *Kaistia granuli* KCTC12575, according to an exemplary embodiment of the present invention.
Figure 4:
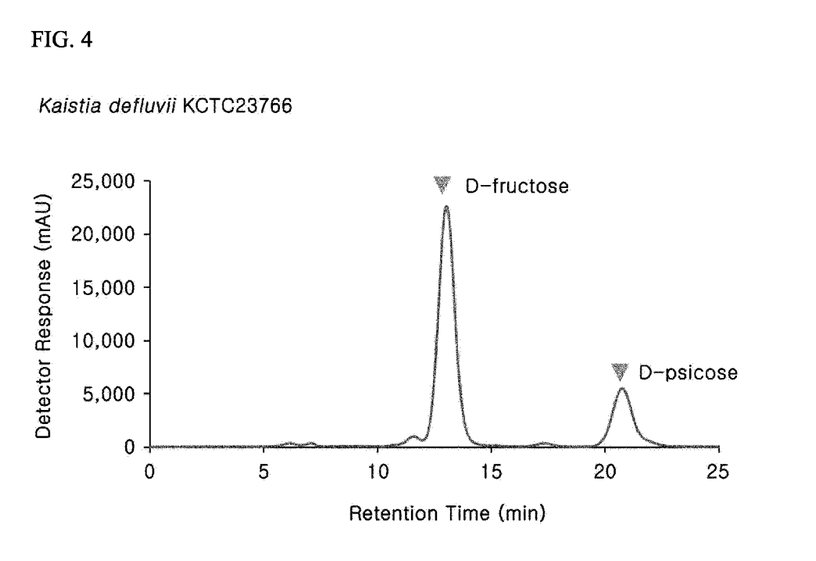
FIG. 4 is HPLC analytical data showing that it is possible to prepare psicose from D-fructose using *Kaistia defluvii* KCTC23766, according to an exemplary embodiment of the present invention.
Figure 5:
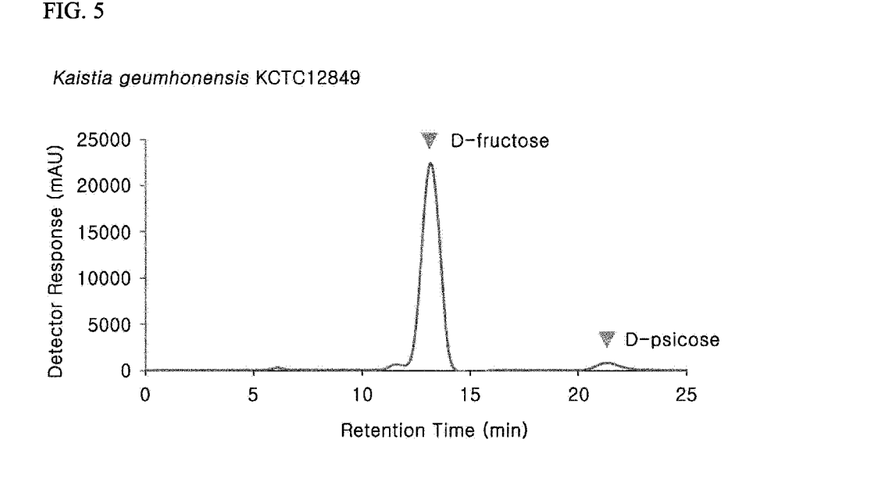
FIG. 5 is HPLC analytical data showing that it is possible to prepare psicose from D-fructose using *Kaistia geumhonensis* KCTC12849, according to an exemplary embodiment of the present invention.
Figure 6:
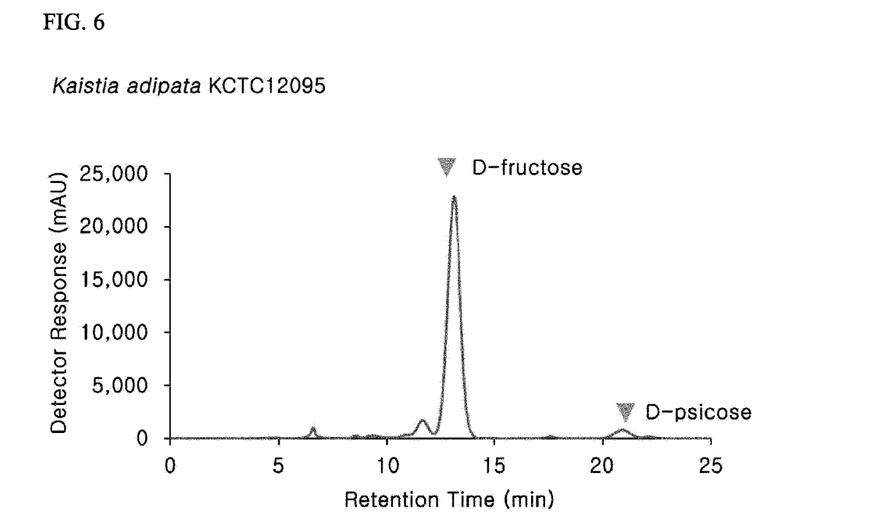
FIG. 6 is HPLC analytical data showing that it is possible to prepare psicose from D-fructose using *Kaistia adipata* KCTC12095, according to an exemplary embodiment of the present invention.
Figure 7:
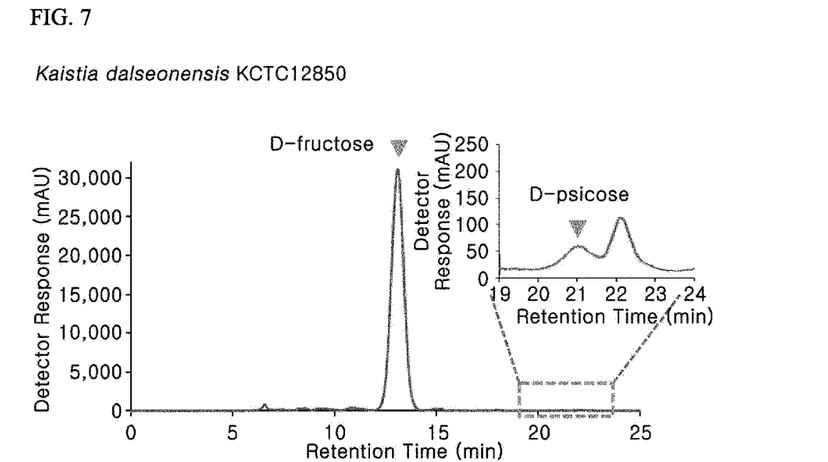
FIG. 7 is HPLC analytical data showing that it is possible to prepare psicose from D-fructose using *Kaistia dalseonensis* KCTC12850, according to an exemplary embodiment of the present invention.
Figure 8:
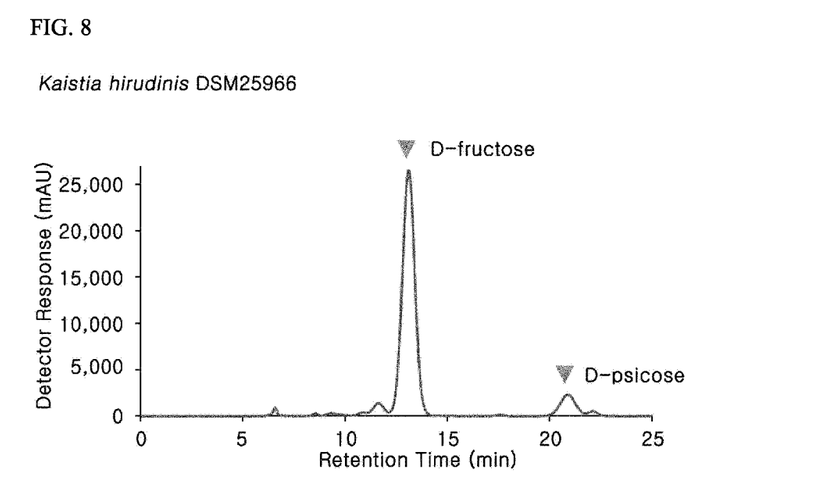
FIG. 8 is HPLC analytical data showing that it is possible to prepare psicose from D-fructose using *Kaistia hirudinis* DSM25966, according to an exemplary embodiment of the present invention.
Figure 9:
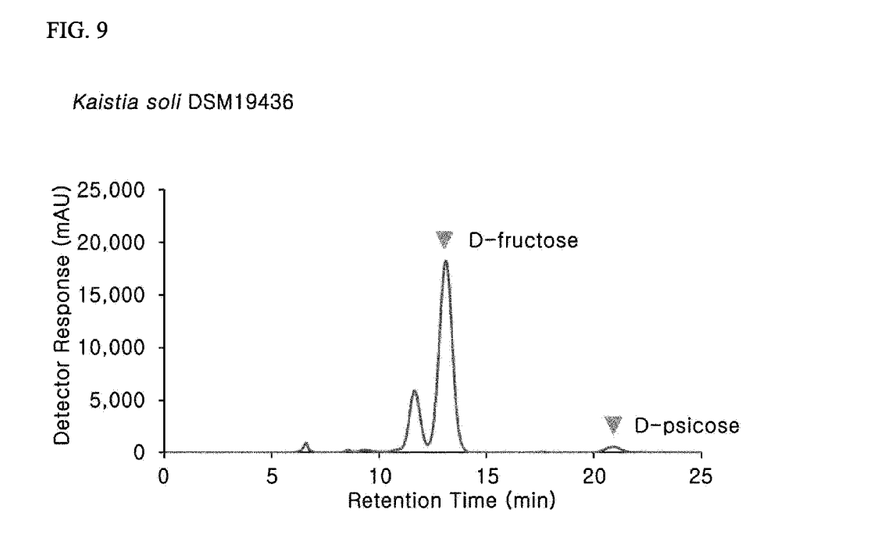
FIG. 9 is HPLC analytical data showing that it is possible to prepare psicose from D-fructose using *Kaistia soli* DSM19436, according to an exemplary embodiment of the present invention.
Figure 10:
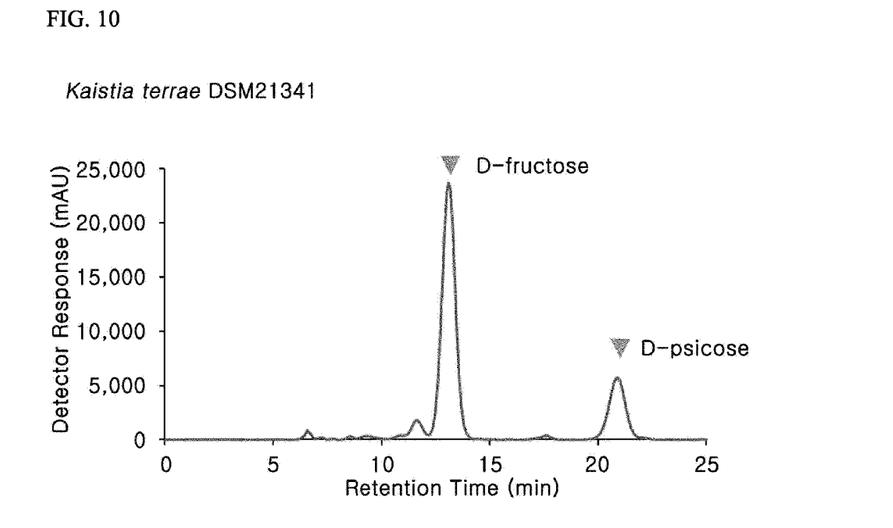
FIG. 10 is HPLC analytical data showing that it is possible to prepare psicose from D-fructose using *Kaistia terrae* DSM21341, according to an exemplary embodiment of the present invention.

Example 1. Isolation of Soil-Born Microorganism that Convert D-Fructose to Psicose To isolate the microorganism that convert D-fructose to psicose, a minimal medium ($KH_2PO_4$ of 2.4 g/L, $K_2HPO_4$ of 5.6 g/L, $(NH_4)_2SO_4$ of 2.6 g/L, 3 mM $MnSO_4$, $7H_2O$ of 0.1 g/L, yeast extract of 1 g/L) to which 1% (w/v) psicose was added was used. 1 g of rhizosphere soil was suspended in 10 mL of 0.85% (w/v) NaCl, and 100 µl of the suspension was plated on an agar medium and cultured at 30° C. Colonies having different shapes and sizes were selected among the colonies formed in the agar medium, and each colony was inoculated into the minimal medium ($KH_2PO_4$ of 2.4 g/L, $K_2HPO_4$ of 5.6 g/L, $(NH_4)_2SO_4$ of 2.6 g/L, 3 mM $MnSO_4$, $7H_2O$ of 0.1 g/L, yeast extract of 1 g/L) and subjected to shaking culture at 30° C. for 24 hours, followed by centrifugation to recover only the cells. The recovered cells were washed with 0.85% (w/v) NaCl, and then, allowed to float by adding 50 mM Tris-Cl buffer (pH 8.0) in which 50% (w/w) D-fructose and 3 mM $MnSO_4$ were added in 20% (w/w) of cell concentration, followed by reaction with the cells at 55° C. for 2 hours. The reaction product was centrifuged to remove the cells the reaction solution, and preparation of the psicose was confirmed by HPLC of the supernatant. The HPLC analysis was performed using HPLC (Agilent, USA) Refractive Index Detector (Agilent 1260 RID) equipped with Aminex HPX-87C column (BIO-RAD), wherein a mobile phase solvent was water, a temperature was 80° C., and a flow rate was 0.6 ml/min. Two kinds of strains (LIS1 and LIS2) that prepared psicose from the D-fructose the most were selected by HPLC analysis (FIGS. 1 and 2).

Base sequences (5' to 3') of the 16s ribosomal DNA of the selected strains LIS1 and LIS2 are as shown in SEQ ID NOs:

1 and 2, respectively. As a result of the sequence homology analysis, SEQ ID NO: 1 showed about 99% homology with the 16s ribosomal DNA sequence (SEQ ID NO: 3) of *Kaistia granuli* Ko04, and SEQ ID NO: 2 showed about 99% homology with the 16s ribosomal DNA sequence (SEQ ID NO: 4) of *Kaistia defluvii* B6-12. Accordingly, the strain LIS1 was identified as of *Kaistia granuli*, and the strain LIS2 was identified as *Kaistia defluvii*, respectively, and named *Kaistia granuli* LIS1 and *Kaistia defluvii* LIS2, respectively. The two strains were deposited in the Korean Culture Center of Microorganisms (KCCM) which is an international depository under the Budapest Treaty, wherein the *Kaistia granuli* LIS1 was deposited on Oct. 20, 2016, and granted accession number KCCM11916P, and the *Kaistia defluvii* LIS2 strain was deposited on Apr. 24, 2017, and granted accession number KCCM12020P.

Example 2. Confirmation of Preparation of Psicose by Microorganism of the Genus *Kaistia*

Whether the psicose could be prepared by the *Kaistia granuli* LIS1, the *Kaistia defluvii* LIS2, other strains of the same species, and a different kind of strain of the genus *Kaistia* was confirmed.

Specifically, eight additional microorganisms (same species: *K. granuli* KCTC12575 and *K. defluvii* KCTC23766; different species: *Kaistia geumhonensis* KCTC12849; *K. dalseonensis* KCTC12850, *K. hirudinis* DSM25966, *K. soli* DSM19436 and *K. terrae* DSM21341) were purchased from the Korean Collection for Type Cultures (KTCT) and Deutsche Sammlung von Mikroorganismen and Zellkulturen inoculated into normal medium (glucose 1 g/L, peptone 15 g/L, NaCl 6 g/L, yeast extract 3 g/L) and subjected to shaking culture at 30° C. for 24 hours, followed by centrifugation to recover only the cells. The recovered cells ere washed with 0.85% (w/v) NaCl and then reacted with 50% (w/w) D-fructose under the same condition as in Example 1 in which the cell concentration was 20% (w/w). After completion of the reaction, the reaction supernatant was analyzed by HPLC to confirm a preparation amount of the psicose. The HPLC analysis was performed in the sale manner as in Example 1. Psicose conversion rate was calculated by the ratio of weight amount of produced psicose after reaction to weight amount of d-fructose before reaction.

As a result, it was confirmed that all of the eight strains of the genus *Kaistia* prepared the psicose from the D-fructose, and this shows that all kinds microorganism of the genus *Kaistia* can produce psicose from D-fructose at a high temperature (table 1, FIGS. 3 to 10).

TABLE 1

| Strain | Conversion rate(%) |
| --- | --- |
| *K. granuli* LIS1 | 28 |
| *K. granuli* KCTC12575 | 25 |
| *K. defluvii* LIS2 | 28 |
| *K. defluvii* KCTC23766 | 23 |
| *K. geumhonensis* KCTC12849 | 11 |
| *K. aditapa* KCTC12095 | 4 |
| *K. dalseonensis* KCTC12850 | 1 |
| *K. hirudinis* DSM25966 | 10 |
| *K. soli* DSM19436 | 4 |
| *K. terrae* DSM21341 | 23 |

From the above description, it will be understood by those skilled in the art that the present invention can be made in other specific forms without modifying a technical idea or essential characteristics thereof. In this regard, it should be understood that the embodiments described above are illustrative in all aspects and not restrictive. The scope of the present invention should be interpreted to cover all modifications or variations derived from the meaning and scope of the appended claims and their equivalents rather than the detailed description.

What is claimed is:

1. A method for preparing D-psicose, comprising: contacting a microorganism of the genus *Kaistia* with D-fructose, wherein D-fructose is converted to D-psicose.

2. The method of claim 1, wherein the microorganism of the genus *Kaistia* is at least one microorganism of the genus *Kaistia* selected from the group consisting of *Kaistia granuli, Kaistia defluvii, Kaistia geumhonensis, Kaistia adipata, Kaistia dalseonensis, Kaistia hirudinis, Kaistia soli* and *Kaistia terrae*.

3. The method of claim 2, wherein the *Kaistia granuli* is *Kaistia granuli* LIS1 strain deposited with Accession number KCCM11916P.

4. The method of claim 2, wherein the *Kaistia defluvii* is *Kaistia defluvii* LIS2 strain deposited with Accession number KCCM12020P.

5. The method of claim 1, wherein the contacting is performed at pH of 5.0 to 9.0, at a temperature of 40° C. to 90° C., or for 0.5 to 48 hours.

* * * * *

SEQUENCE LISTING

<160> NUMBER OF SEQ ID NOS: 4

<210> SEQ ID NO 1
<211> LENGTH: 1401
<212> TYPE: DNA
<213> ORGANISM: Unknown
<220> FEATURE:
<223> OTHER INFORMATION: Kaistia granuli LIS1

<400> SEQUENCE: 1

| | | | | | |
|---|---|---|---|---|---|
| aggggggttgg | cggcaggcct | accatgcaag | tcgacgccct | agcaataggg | agtggcagac | 60 |
| gggtgagtaa | cgcgtgggaa | tctaccttgt | ggtacggaac | aaccaaggga | aactttggct | 120 |
| aataccgtat | gagcccttcg | ggggaaagat | ttatcgccat | aagatgagcc | cgcgtaggat | 180 |
| tagctagttg | gtgaggtaat | ggctcaccaa | ggcgacgatc | cttagctggt | ctgagaggat | 240 |
| gaccagccac | actgggactg | agacacggcc | cagactccta | cgggaggcag | cagtggggaa | 300 |
| tattggacaa | tgggcgcaag | cctgatccag | ccatgccgcg | tgtgtgatga | aggccttagg | 360 |
| gttgtaaagc | actttcgccg | atgaagataa | tgactgtagt | cggagaagaa | gccccggcta | 420 |
| acttcgtgcc | agcagccgcg | gtaatacgaa | ggggggctagc | gttgttcgga | attactgggc | 480 |
| gtaaagcgta | cgtaggcgga | tcgttaagtt | aggggtgaaa | tcccgaggct | caacctcgga | 540 |
| actgcctctg | atactggcga | tcttgagtcc | gggagaggtg | agtggaactc | ctagtgtaga | 600 |
| ggtgaaattc | gtagatatta | ggaagaacac | cagtggcgaa | ggcggctcac | tggcccggaa | 660 |
| ctgacgctga | ggtacgaaag | cgtggggagc | aaacaggatt | agataccctg | gtagtccacg | 720 |
| ccgtaaacga | tggatgctag | ccgtcgggga | gcttgctctt | cggtggcgca | gctaacgcat | 780 |
| taagcatccc | gcctggggag | tacggtcgca | agattaaaac | tcaaaggaat | tgacgggggc | 840 |
| ccgcacaagc | ggtggagcat | gtggtttaat | tcgaagcaac | gcgcagaacc | ttaccagctc | 900 |
| ttgacatgtc | acgtatgggt | accggagacg | gtatccttca | gttcggctgg | cgtgaacaca | 960 |
| ggtgctgcat | ggctgtcgtc | agctcgtgtc | gtgagatgtt | gggttaagtc | ccgcaacgag | 1020 |
| cgcaaccctc | gcctctagtt | gccatcattc | agtttgggcac | tctagaggga | ctgccggtga | 1080 |
| taagccgaga | ggaaggtggg | gatgacgtca | agtcctcatg | gcccttacgg | gctgggctac | 1140 |
| acacgtgcta | caatggcggt | gacaatgggc | agcgaaaggg | cgacctggag | ctaatctcaa | 1200 |
| aaagccgtct | cagttcggat | tgcactctgc | aactcgagtg | catgaagttg | gaatcgctag | 1260 |
| taatcgtgga | tcagcatgcc | acggtgaata | cgttcccggg | ccttgtacac | accgcccgtc | 1320 |
| acaccatggg | agttggtttt | acccgaaggc | gttgcgctaa | cccagcaatg | gaggcaggcg | 1380 |
| acctctaaag | taactactgt | g | | | | 1401 |

<210> SEQ ID NO 2
<211> LENGTH: 1398
<212> TYPE: DNA
<213> ORGANISM: Unknown
<220> FEATURE:
<223> OTHER INFORMATION: Kaistia defluvii LIS2

<400> SEQUENCE: 2

| | | | | | |
|---|---|---|---|---|---|
| gtgctatcgg | gtacgctaag | atgcttatgg | ctcaccctgg | ctacagggag | tggcagacgg | 60 |
| gtgagtaacg | cgtgggaatc | taccttgtgg | tacggaacaa | ccaagggaaa | ctttggctaa | 120 |
| taccgtatga | gcccttcggg | ggaaagattt | atcgccataa | gatgagcccg | cgtaggatta | 180 |
| gctagttggt | gaggtaatgg | ctcaccaagg | cgacgatcct | tagctggtct | gagaggatga | 240 |
| ccagccacac | tgggactgag | acacggccca | gactcctacg | ggaggcagca | gtggggaata | 300 |

-continued

```
ttggacaatg ggcgcaagcc tgatccagcc atgccgcgtg tgtgatgaag gccttagggt        360
tgtaaagcac tttcgccgat gaagataatg actgtagtcg gagaagaagc cccggctaac        420
ttcgtgccag cagccgcggt aatacgaagg gggctagcgt tgttcggaat tactgggcgt        480
aaagcgtacg taggcggatt gttaagtgag gggtgaaatc ccgaggctca acctcggaac        540
tgcctttcat actggcaatc ttgagtccgg gagaggtgag tggaactcct agtgtagagg        600
tgaaattcgt agatattagg aagaacacca gtggcgaagg cggctcactg gcccggaact        660
gacgctgagg tacgaaagcg tggggagcaa acaggattag ataccctggt agtccacgcc        720
gtaaacgatg gatgctagcc gtcggggagc ttgctcttcg gtggcgcagc taacgcatta        780
agcatcccgc ctgggagta cggtcgcaag attaaaactc aaaggaattg acggggaccc        840
gcacaagcgg tggagcatgt ggtttaattc gaagcaacgc gcagaacctt accagctctt        900
gacatgtcac gtatgggtac cggagacggt attcttcagt tcggctggcg tgaacacagg        960
tgctgcatgg ctgtcgtcag ctcgtgtcgt gagatgttgg gttaagtccc gcaacgagcg       1020
caaccctcgc ccttagttgc catcattcag ttgggcactc taggggact gccggtgata       1080 agccgagagg aaggtgggga tgacgtcaag tcctcatggc ccttacgggc tgggctacac       1140
acgtgctaca atggcggtga caatgggcag cgaaggggcg acctggagct aatctcaaaa       1200
aaccgtctca gttcggattg cactctgcaa ctcgagtgca tgaagttgga atcgctagta       1260
atcgtggatc agcatgccac ggtgaatacg ttcccgggcc ttgtacacac cgcccgtcac       1320
accatgggag tcggttttac ctgtaggcgt tgcgctaacc cagcaagcgt aacaggcgac       1380
cacgaaagga gtaccata                                                    1398
```

<210> SEQ ID NO 3
<211> LENGTH: 1429
<212> TYPE: DNA
<213> ORGANISM: Unknown
<220> FEATURE:
<223> OTHER INFORMATION: Kaistia granuli strain Ko04

<400> SEQUENCE: 3

```
ccccgtagaa cgaacgctgg cggcaggcct aacacatgca agtcgaacgc cctagcaata         60
gggagtggca gacgggtgag taacgcgtgg gaatctacct tgtggtacgg aacaaccaag        120 ggaactttg gctaataccg tatgagccct tcggggaaa gatttatcgc cataagatga         180
gcccgcgtag gattagctag ttggtgaggt aatggctcac caaggcgacg atccttagct        240
ggtctgagag gatgaccagc cacactggga ctgagacacg gcccagactc ctacgggagg        300
cagcagtggg gaatattgga caatgggcgc aagcctgatc cagccatgcc gcgtgtgtga        360
tgaaggcctt aggttgtaa agcactttcg ccgatgaaga taatgactgt agtcggagaa        420
gaagccccgg ctaacttcgt gccagcagcc gcggtaatac gaagggggct agcgttgttc        480
ggaattactg ggcgtaaagc gtacgtaggc ggatcgttaa gttagggtg aaatcccgag        540 gctcaacctc ggaactgcct ctgatactgg cgatcttgag tccgggagag gtgagtggaa        600
ctcctagtgt agaggtgaaa ttcgtagata ttaggaagaa caccagtggc gaaggcggct        660
cactggcccg gaactgacgc tgaggtacga aagcgtgggg agcaaacagg attagatacc        720
ctggtagtcc acgccgtaaa cgatggatgc tagccgtcgg ggagcttgct cttcggtggc        780
gcagctaacg cattaagcat cccgcctggg gagtacggtc gcaagattaa aactcaaagg        840
aattgacggg ggcccgcaca agcggtggag catgtggttt aattcgaagc aacgcgcaga        900
```

```
accttaccag ctcttgacat gtcacgtatg ggtaccggag acggtatcct tcagttcggc      960
tggcgtgaac acaggtgctg catggctgtc gtcagctcgt gtcgtgagat gttgggttaa     1020
gtcccgcaac gagcgcaacc ctcgcctcta gttgccatca ttcagttggg cactctagag     1080
ggactgccgg tgataagccg agaggaaggt ggggatgacg tcaagtcctc atggccctta    1140
cgggctgggc tacacacgtg ctacaatggc ggtgacaatg ggcagcgaaa gggcgacctg     1200
gagctaatct caaaaagccg tctcagttcg gattgcactc tgcaactcga gtgcatgaag     1260
ttggaatcgc tagtaatcgt ggatcagcat gccacggtga atacgttccc gggccttgta     1320
cacaccgccc gtcacaccat gggagttggt tttacccgaa ggcgttgcgc taacccagca     1380
atgggaggca ggcgaccacg gtagggtcag cgacttgggg tgacaaaaa                1429
```

<210> SEQ ID NO 4
<211> LENGTH: 1456
<212> TYPE: DNA
<213> ORGANISM: Unknown
<220> FEATURE:
<223> OTHER INFORMATION: Kaistia defluvii strain B6-12

<400> SEQUENCE: 4

```
tcagaacgaa cgctggcggc aggcctaaca catgcaagtc gaacgccctg caacaggga       60 gtggcagacg ggtgagtaac gcgtgggaat ctaccttgtg gtacggaaca accaagggaa     120
actttggcta ataccgtatg agcccttcgg gggaaagatt tatcgccata agatgagccc     180
gcgtaggatt agctagttgg tgaggtaatg gctcaccaag gcgacgatcc ttagctggtc     240
tgagaggatg accagccaca ctgggactga gacacggccc agactcctac gggaggcagc     300
agtggggaat attggacaat gggcgcaagc ctgatccagc catgccgcgt gtgtgatgaa     360
ggccttaggg ttgtaaagca ctttcgccga tgaagataat gactgtagtc ggagaagaag     420
ccccggctaa cttcgtgcca gcagccgcgg taatacgaag gggctagcg ttgttcggaa     480 ttactgggcg taaagcgtac gtaggcggat tgttaagtga ggggtgaaat cccgaggctc     540
aacctcggaa ctgccttca tactggcaat cttgagtccg ggagaggtga gtggaactcc      600
tagtgtagag gtgaaattcg tagatattag gaagaacacc agtggcgaag gcggctcact     660
ggcccggaac tgacgctgag gtacgaaagc gtggggagca acaggatta gataccctgg      720 tagtccacgc cgtaaacgat ggatgctagc cgtcggggag cttgctcttc ggtgcgcag      780 ctaacgcatt aagcatcccg cctggggagt acggtcgcaa gattaaaact caaaggaatt     840
gacgggggcc cgcacaagcg gtggagcatg tggtttaatt cgaagcaacg cgcagaacct     900
taccagctct tgacatgtca cgtatgggta ccggagacgg tattcttcag ttcggctggc     960
gtgaacacag gtgctgcatg gctgtcgtca gctcgtgtcg tgagatgttg ggttaagtcc    1020
cgcaacgagc gcaaccctcg cccttagttg ccatcattca gttgggcact ctaggggac     1080 tgccggtgat aagccgagag gaaggtgggg atgacgtcaa gtcctcatgg cccttacggg    1140
ctgggctaca cacgtgctac aatgcggtg acaatgggca gcgaagggc gacctggagc     1200 taatctcaaa aaccgtctc agttcggatt gcactctgca actcgagtgc atgaagttgg     1260
aatcgctagt aatcgtggat cagcatgcca cggtgaatac gttcccgggc cttgtacaca    1320
ccgcccgtca caccatggga gttggtttta cccgaaggcg ttgcgctaac ccagcaatgg    1380
gaggcaggcg accacggtag ggtcagcgac tggggtgaag tcgtaacaag gtagccgtag    1440 gggaaccctgc ggctgg                                                    1456
```